United States Patent [19]

Nakane et al.

[11] 4,416,896
[45] Nov. 22, 1983

[54] 7-OXABICYCLOHEPTANE SUBSTITUTED AMINO PROSTAGLANDIN ANALOGS USEFUL IN THE TREATMENT OF THROMBOLYTIC DISEASE

[75] Inventors: Masami Nakane, Plainsboro, N.J.; David L. Snitman, Boulder, Colo.; Joyce Reid, Dayton; Martin F. Haslanger, Lambertville, both of N.J.

[73] Assignee: E. R. Squibb & Sons, Inc., Princeton, N.J.

[21] Appl. No.: 378,560

[22] Filed: May 17, 1982

[51] Int. Cl.$^3$ .................... A61K 31/34; C07D 307/00
[52] U.S. Cl. .................................... 424/285; 549/463
[58] Field of Search ...................... 549/463; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/459 |
| 4,228,180 | 10/1980 | Sprague | 549/463 |
| 4,254,044 | 3/1981 | Sprague | 549/463 |

FOREIGN PATENT DOCUMENTS 43292  6/1982  European Pat. Off.
2039909  8/1980  United Kingdom.

Primary Examiner—Henry R. Jiles
Assistant Examiner—Bernard Dentz
Attorney, Agent, or Firm—Lawrence S. Levinson; Burton Rodney

[57] ABSTRACT

7-Oxabicycloheptane substituted amino prostaglandin analogs are provided having the structural formula

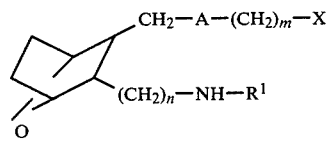

and including all stereoisomers thereof.

The compounds are cardiovascular agents useful, for example, in the treatment of thrombolytic disease.

15 Claims, No Drawings

7-OXABICYCLOHEPTANE SUBSTITUTED AMINO PROSTAGLANDIN ANALOGS USEFUL IN THE TREATMENT OF THROMBOLYTIC DISEASE

DESCRIPTION OF THE INVENTION

The present invention relates to 7-oxabicycloheptane alkylamino- and other substituted amino prostaglandin analogs which are cardiovascular agents useful, for example, in the treatment of thrombolytic disease. These compounds have the structural formula

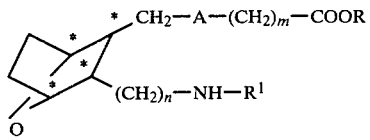

and including all stereoisomers thereof, wherein

A is CH=CH or $(CH_2)_2$; m is 1 to 8; n is 0 to 5, R is H or lower alkyl; and $R^1$ is lower alkyl, aryl, aralkyl, lower alkoxy, aralkoxy or

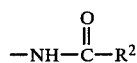

wherein $R^2$ is lower alkyl, aryl, aralkyl, alkoxy, aryloxy, aralkoxy, alkylamino, arylamino or aralkylamino.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The terms "$(CH_2)_m$" and "$(CH_2)_n$" includes a straight or branched chain radical having from 1 to 8 carbons in the normal chain in the case of "$(CH_2)_m$" and 0 to 5 carbons in the normal chain in the case of "$(CH_2)_n$" and may contain one or more lower alkyl substituents. Examples of $(CH_2)_m$ and $(CH_2)_n$ groups include $CH_2$, $CH_2CH_2$, $(CH_2)_3$, $(CH_2)_4$, $(CH_2)_5$, $(CH_2)_6$, $(CH_2)_7$,

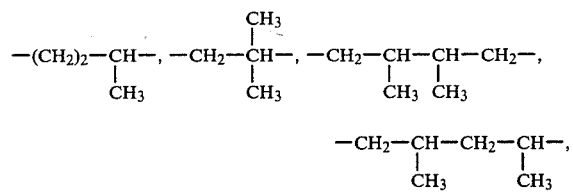

and the like.

Preferred are those compounds of formula I wherein A is $(CH_2)_2$ or CH=CH, m is 2 to 4, R is H, n is 0 or 1, and $R^1$ is phenyloxy, pentyloxy, pentyl, hexyl or heptyl,

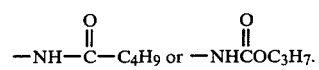

The various compounds of the invention may be prepared as outlined below.

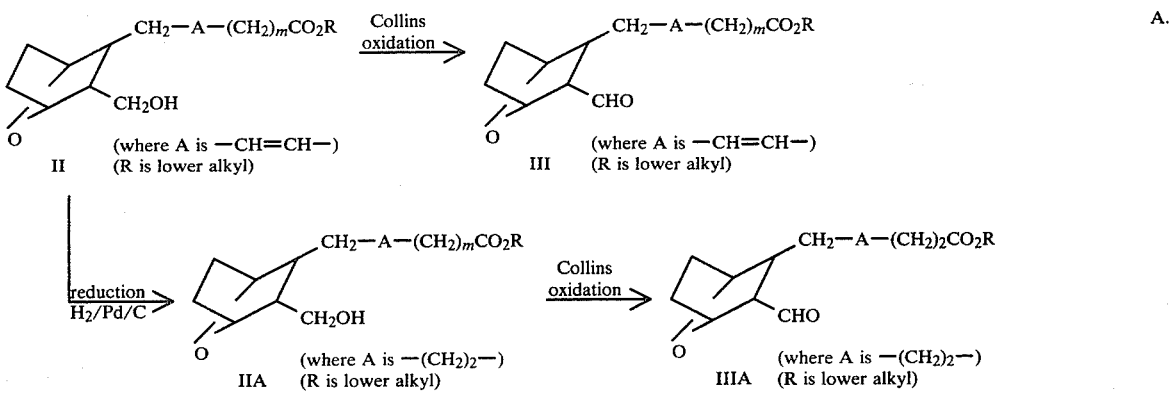

A.

Where n is 1 and $R^1$ is lower alkyl

B.

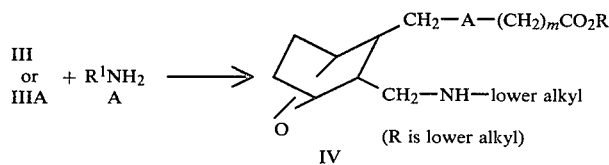
Where n is 1 and $R^1$ is $-O(CH_2)_p R^3$ where $R^3$ is alkyl or aralkyl and p is 1 to 5, that is, lower alkoxy or aralkoxy    C.
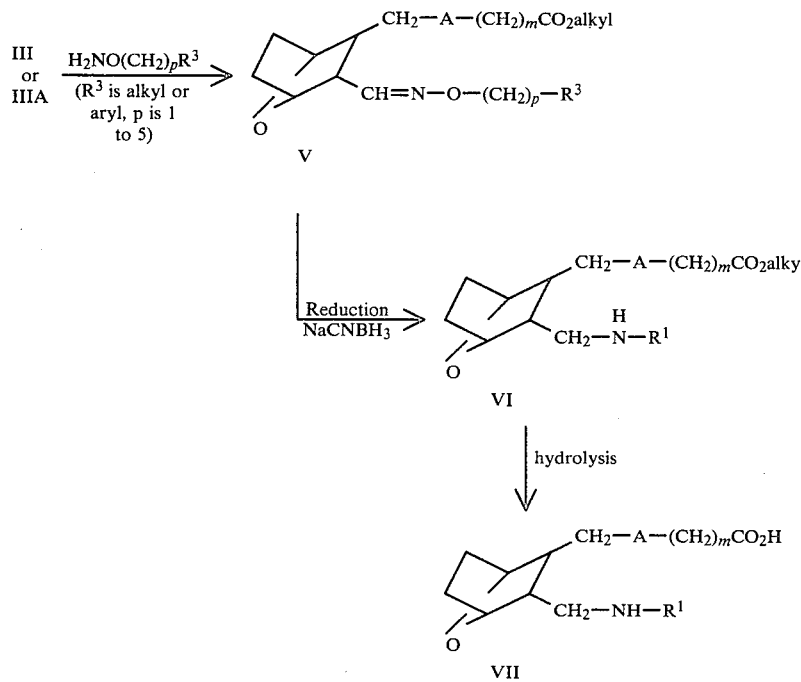
Where n is 1 and $R^1$ is $-NH-\overset{O}{\underset{\|}{C}}-R^2$    D.
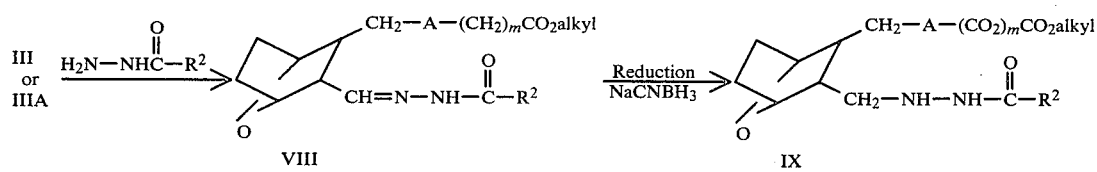
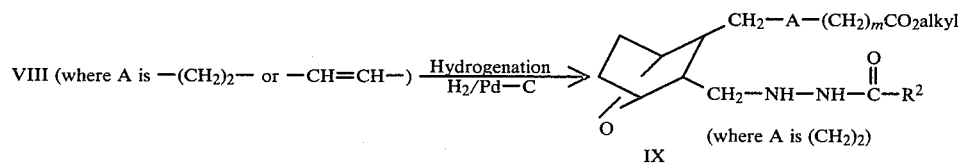
Where n is 0 and $R^1$ is $-NH-$alkyl    E.

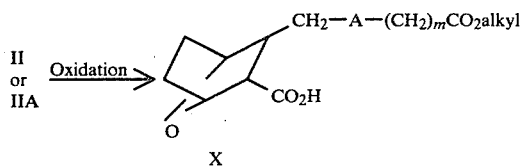 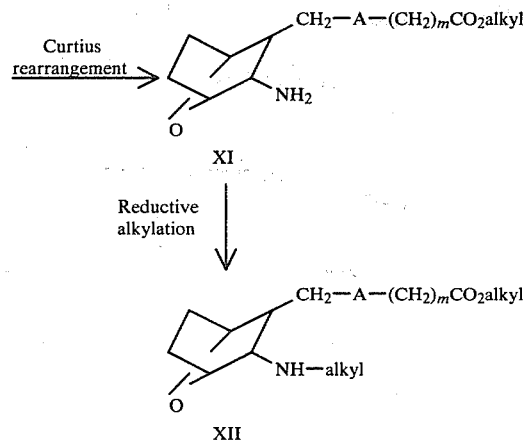

In the reaction sequence identified as "A", the starting lower alkyl ester containing the hydroxymethyl group, that is, compound II, (prepared as described in U.S. Pat. No. 4,143,054) is used to form the aldehyde III (where A is —CH=CH—) or IIIA (where A is —(CH$_2$)$_2$). Thus, to form aldehyde III where A is —CH=CH—, compound II is subjected to a Collins oxidation, for example, by reacting II with chromium trioxide in pyridine. To form the aldehyde IIIA (where A is (CH$_2$)$_2$), compound II is reduced, for example with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$).

As seen in reaction sequence "B", compounds of the invention where n is 1 and R$^1$ is lower alkyl, that is

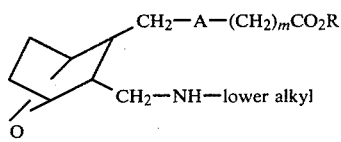

are prepared by reacting aldehyde III or IIIA with an alkylamine (R$^1$NH$_2$) employing a molar ratio of III or IIIA:alkylamine of within the range of from about 0.8:1 to about 1:1, in a solvent such as methanol or ethanol and a reducing agent such as sodium borohydride or sodium cyanoborohydride.

As seen in reaction sequence "C", compounds of the invention wherein n is 1 and R$^1$ is lower alkoxy or aralkoxy, that is

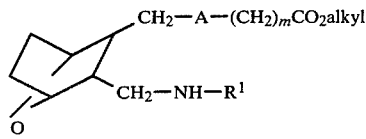

are prepared by reacting aldehyde III or IIIA with an oxyamine, such as of the structure B.   H$_2$NO(CH$_2$)$_p$R$^3$    (p is 1 to 5)

employing a molar ratio of III or IIIA:B of within the range of from about 0.8:1 to about 1:1 in a solvent such as methanol or ethanol.

Compound V is then reduced, such as by reacting V with a reducing agent such as NaBH$_4$ or NaCNBH$_3$ in a solvent such as methanol or ethanol and in the presence of acetic acid to form the compound of structure VI.

Where p is 0 so that R$^1$ is aryloxy, then compound II or IIA is first hydrolyzed by reacting same with lithium hydroxide or sodium hydroxide to form the corresponding carboxylic acid IIB

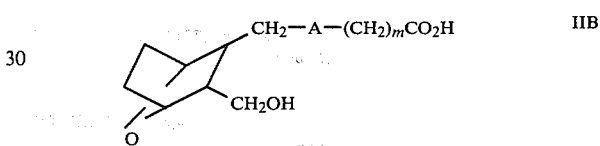

(where A is —(CH$_2$)$_2$— or —CH=CH—)
which is then subjected to a Collins oxidation (as described above) to form the corresponding aldehyde IIIB

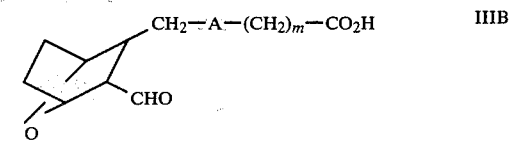

Aldehyde IIIB is reacted with an aryloxyamine B'
B'     H$_2$NO(CH$_2$)$_p$R$^3$
(where p is 0 and R$^3$ is aryl)
to form the compound VA

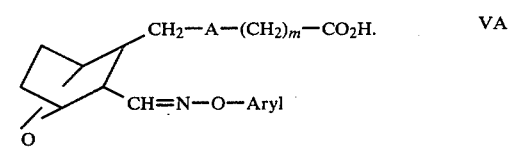

Compound VA is then reduced with NaCNBH$_3$ in the presence of acetic acid to form the aryloxyamine of the invention

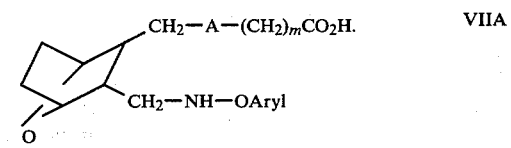

In the reaction sequence identified as "D", compounds of the invention wherein n is 1 and R¹ is

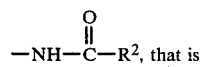, that is    IX

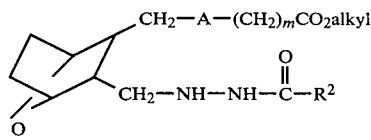

are prepared by reacting aldehyde III or IIIA with a hydrazine derivative

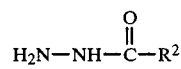    C.

to form compound VIII, employing a molar ratio of III or IIIA:C of within the range of from about 0.8:1 to about 1:1, in a protic solvent such as methanol or ethanol.

Compound VIII is then reduced, such as by reacting VIII with a reducing agent, such as NaBH₃CN or NaBH₄ in the presence of acetic acid or hydrogen with palladium on carbon as a catalyst to form compound IX.

Compound IX where A is —(CH₂)₂— or —CH═CH— may also be prepared by subjecting compound VIII (where A is —(CH₂)₂— or —CH═CH—) to hydrogenation by reacting VIII with hydrogen gas over a palladium on carbon catalyst.

In the reaction sequence identified as "E", compounds of the invention wherein n is 0 and R¹ is —NH—alkyl, that is

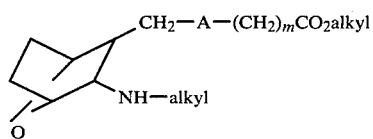    XII are prepared by oxidizing hydroxymethyl compound II or IIA, such as by reacting II or IIA with an oxidizing agent, such as pyridinium dichromate in a solvent, such as dimethylformamide, to form the acid X. Acid X is subjected to a Curtius rearrangement reaction which involves reacting acid X with carbonyldiimidazole in the presence of an inert organic solvent, such as toluene, under an inert atmosphere, followed by addition of trimethylsilylazide to the reaction mixture and the resulting isocyanate solution is converted to the amine XI by reacting same with hydrochloric acid.

The amine XI is subjected to reductive alkylation by reacting same with heptanal in a solvent, such as methanol and then adding sodium borohydride or other reducing agent, such as sodium cyanoborohydride in the presence of acetic acid to form the compound XII.

The esters IV, VI, IX and XII can be converted to the free acid, that is, to

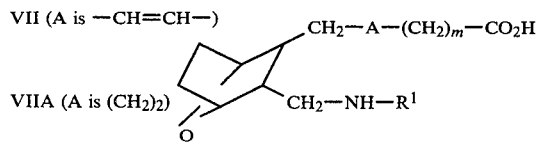

by treating the esters with a base, such as lithium hydroxide, followed by neutralization with an acid, such as dilute hydrochloric acid or oxalic acid.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis exo, cis endo and all trans forms and stereoisomeric pairs may be prepared as shown in the working Examples which follow and by employing starting materials and following the procedures as outlined in U.S. Pat. No. 4,143,054. Examples of such stereoisomers are set out below.

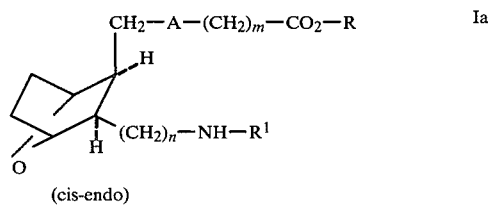

(cis-endo)

(cis-exo)

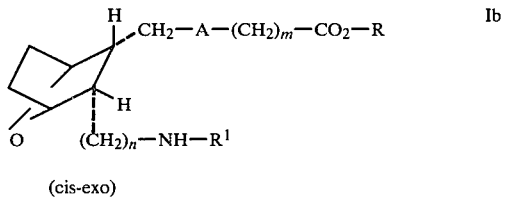

(trans)

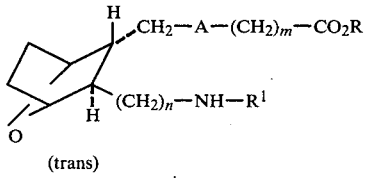

(trans)

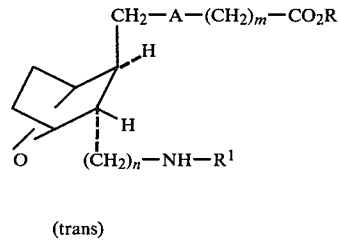

The nucleus in each of the compounds of the invention is depicted as

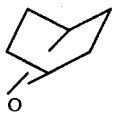

for matter of convenience; it will also be appreciated that the nucleus in the compounds of the invention may be depicted as

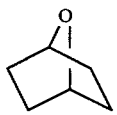

The compounds of this invention are cardiovascular agents useful as platelet aggregation inhibitors, e.g., for treatment of thrombolytic disease, such as coronary or cerebral thromboses. They are also selective thromboxane $A_2$ receptor antagonists and synthetase inhibitors, e.g., having a vasodilatory effect for treatment of myocardial ischemic disease, such an angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of this invention.

EXAMPLE 1

[1β,2α(5Z),3β,4β]-7-[3-[(Hexylamino)methyl]-7-oxabicyclo[2.2.1]hept-2-yl]-5-heptenoic acid

A.

[1β,2α(5Z),3β,4β]-7-[3-Formyl-7-oxabicyclo[2.2.1]hept-2-yl]-5-heptenoic acid, methyl ester A solution of pyridine (14.6 ml) in dichloromethane (500 ml) was treated portionwise with chromium trioxide (9.06 g) with vigorous stirring. After addition was complete, the mixture was stirred at room temperature for 30 minutes then treated with celite (30 g) then [1β,2α(5Z),3β,4β]-7-[3-(hydroxymethyl)-7-oxabicyclo[2.2.1]hept-2-yl]-5-heptenoic acid, methyl ester prepared as described in U.S. Pat. No. 4,143,054 (4.05 g, 15.1 mmoles) in dichloromethane (25 ml). The reaction mixture was stirred at room temperature for 30 minutes then filtered through celite. The filtrate was washed with 5% sodium bicarbonate (2×300 ml), 10% hydrochloric acid (2×300 ml) and again with 5% sodium bicarbonate (1×300 ml). The dichloromethane solution was dried over magnesium sulfate and concentrated in vacuo. The residue was dissolved in ether, and filtered through a pad of Baker silica gel, washed with ether and the filtrate taken to dryness in vacuo leaving 3.79 g (92%) of pale yellow oil.

B. [1β,2α(5Z), 3β,4β]-7-[3-[(Hexylamino)methyl]-7-oxabicyclo[2.2.1]hept-2-yl]-5-heptenoic acid, methyl ester To 134 mg (0.50 mmole, 1 eq) of the title A aldehyde in 3 ml of anhydrous methanol under an argon atmosphere at 25° was added 101.1 mg (1.0 mmole, 2 eq) of hexylamine and ca. 300 mg of activated crushed 3 Å molecular sieves. The reaction was stirred for 96 hours, diluted with 2 ml of anhydrous methanol, cooled to 0° and an excess of sodium borohydride was added. This reaction mixture was stirred for 30 minutes, quenched with 1 ml of acetone, diluted with 100 ml of ether and washed successively with 50 ml of water and 50 ml of brine, and dried over anhydrous magnesium sulfate. The product was purified by flash chromatography on LP-1 silica using a 167/15/1 chloroform:methanol:formic acid solution as the eluent to provide 150 mg (85%) of the title compound as an oil.

C. [1β,2α(5Z),3β,4β]-7-[3-[(Hexylamino)methyl]-7-oxabicyclo[2.2.1]hept-2-yl]-5-heptenoic acid 150 mg (0.43 mmol) of the title B ester in 10 ml of a 1 N sodium hydroxide solution was refluxed for 45 minutes, cooled, neutralized to ca. pH 6.5 with dilute hydrochloric acid, and extracted with two 85 ml portions of ethyl acetate to provide 85 mg of a yellow oil. This material was recrystallized twice from acetonitrile to provide 53.6 mg (37%) of the title product as an off-white crystalline solid: m.p. 99–100.5.

Analysis Calcd for: C, 71.17; H, 10.45; N, 4.15 Found: C, 70.76; H, 10.41; N, 4.23

EXAMPLE 2

[1β,2α(5Z),3α,4β]-7-[3-[(Hexylamino)methyl]-7-oxabicyclo[2.2.1]hept-2-yl]-5-heptenoic acid

A.

[1β,2α(5Z),3α,4β]-7-[3-Formyl-7-oxabicyclo[2.2.1]hept-2-yl]-5-heptenoic acid, methyl ester A solution of pyridine (14.3 ml, 177 mmol) in dichloromethane (500 ml) was treated portionwise with chromium trioxide (8.9 g, 8.9 mmoles) with vigorous stirring. After addition was complete, the mixture was stirred at room temperature for 30 minutes then treated with celite (30 g) then [1β,2α(5Z),3α,4β]-7-[3-(hydroxymethyl)-7-oxabicyclo[2.2.1]hept-2-yl]-5-heptenoic acid, methyl ester prepared as described in U.S. Pat. No. 4,143,054 (4 g, 14.96 mmoles) in dichloromethane (20 ml) was added dropwise over a 20 minute period. The reaction mixture was stirred at room temperature for 30 minutes then filtered through celite. The filtrate was washed with 5% sodium bicarbonate (2×250 ml), 10% hydrochloric acid (2×100 ml) and again with 5% sodium bicarbonate (2×250 ml)

The dichloromethane solution was dried over magnesium sulfate, filtered and concentrated in vacuo. A brownish residue was dissolved in ether and passed through a pad of Baker silica gel, then eluted with more ether and the ether solution was taken to dryness in vacuo leaving 3.86 g of colorless oil.

B.
[1β,2α(5Z),3α,4β]-7-[3-[(Hexylamino)methyl]-7-oxabicyclo[2.2.1]hept-2-yl]-5-heptenoic acid, methyl ester The title A aldehyde was treated with hexylamine as described in Example 1B to give [1β,2α(5Z),3α,4β]-7-[3-[(hexylamino)methyl]-7-oxabicyclo[2.2.1]hept-2-yl]-5-heptenoic acid, methyl ester.

C.
[1β,2α(5Z),3α,4β]-7-[3-[(Hexylamino)methyl]-7-oxabicyclo[2.2.1]hept-2-yl]-5-heptenoic acid 150 mg (0.43 mmole) of the title B ester in 10 ml of a 1 N sodium hydroxide solution is refluxed for 45 minutes, cooled, neutralized to ca. pH 6.5 with dilute hydrochloric acid, and extracted with two 85 ml portions of ethyl acetate to provide 85 mg of a yellow oil. This material is recrystallized twice from acetonitrile to provide 53.6 mg (37%) of the title product as an off-white crystalline solid.

EXAMPLE 3

(1β,2β,3α,4β)-7-[3-[(Hexylamino)methyl]-7-oxabicyclo[2.2.1]hept-2-yl]heptanoic acid

A.
(1β,2β,3β,4β)-7-[3-(Hydroxymethyl)-7-oxabicyclo[2.2.1]hept-2-yl]-heptanoic acid, methyl ester To 800 mg (3.0 mmole) of the [1β,2β(5Z),3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.
(1β,2β,3β,4β)-7-[3-Formyl-7-oxabicyclo[2.2.1]hept-2-yl]heptanoic acid, methyl ester To 1.21 g (5.6 mmole, 2.0 equiv.) of pyridiniumchlorochromate (PCC) and 20 ml of anhydrous $CH_2Cl_2$ was added, under an argon atmosphere, 730 mg (2.8 mmole) of the title A alcohol in 2 ml of $CH_2Cl_2$. The reaction was stirred for 2 hours at 25°, diluted with 100 ml of ether, filtered through a pad of florisil, and evaporated to furnish 670 mg (88%) of the title B compound as a white crystalline solid.

C.
(1β,2β,3α,4β)-7-[3-Formyl-7-oxabicyclo[2.2.1]hept-2-yl]heptanoic acid, methyl ester To 800.0 mg of the title B aldehyde in 20 ml of anhydrous methanol under an argon atmosphere at 25° was added 100 mg of sodium methoxide. The reaction was stirred for 2 hours, diluted with 100 ml of saturated ammonium chloride and extracted with four 100 ml portions of ether. The ethereal layer was washed with 50 ml of brine dried oer anhydrous magnesium sulfate and concentrated to afford 765.0 mg (98%) of the title C aldehyde.

D.
(1β,2β,3α,4β)-7-[3-[(Hexylamino)methyl]-7-oxabicyclo[2.2.1]hept-2-yl]heptanoic acid Following the procedure of Example 1, except substituting the Part C aldehyde for the Example 1A aldehyde, the title product is obtained.

EXAMPLE 4

[1β,2α(5Z),3α,4β]-7-[3-[[(Phenylmethoxy)amino]methyl]-7-oxabicyclo[2.2.1]hept-2-yl]-5-heptenoic acid

A.
[1β,2α(5Z),3α,4β]-7-[3-[[(Phenylmethoxy)imino]methyl]-7-oxabicyclo[2.2.1]hept-2-yl]-5-heptenoic acid, methyl ester NaOAc (164 mg, 2 mmol) was added to a magnetically stirred suspension of O-benzylhydroxylamine hydrochloride (320 mg, 2 mmol) in EtOH (8 ml) at room temperature. Then, [1β,2α(5Z),3α,4β]-7-[3-formyl-7-oxabicyclo[2.2.1]hept-2-yl]-5-heptenoic acid, methyl ester prepared as described in Example 2, Part A (532 mg, 2 mmol) in EtOH (2 ml) was added and stirred for 1 hour at room temperature. The reaction was poured into $Et_2O$ (100 ml), which was washed with 1 N HCl (20 ml×2), saturated $NaHCO_3$ (20 ml×2), brine (20 ml×2), and dried over $MgSO_4$. Filtration and evaporation of solvents gave the title compound in the form of a colorless oil (825 mg), which was purified by a silica gel column (silica 60, 30 g) eluted with $Et_2O$/pet ether (2/3) to give anti isomer (592 mg, 1.59 mmol) and a mixture of syn and anti isomers (125 mg, 0.336 mmol).

B.
[1β,2α(5Z),3α,4β]-7-[3-[[(Phenylmethoxy)amino]methyl]-7-oxabicyclo[2.2.1]hept-2-yl]-5-heptenoic acid, methyl ester $NaBH_3CN$ (57 mg, 0.92 mmol) was added to a magnetically stirred solution of oxime prepared as described in Part A (265 mg, 0.71 mmol) in MeOH (8.5 ml), followed by addition of AcOH (1.5 ml) dropwise. After 2¼ hours stirring at room temperature, additional $NaBH_3CN$ (40 mg, 0.64 mmol) and AcOH (1 ml) were added. Stirring was continued at room temperature for 1 hour. Then, the reaction was quenched by addition of 2 N HCl to pH 1 and stirred for 30 minutes. The reaction was basicified by addition of saturated $NaHCO_3$. The products were extracted with $Et_2O$ (100 ml×2). The combined ether layers were washed with brine and dried over $MgSO_4$. Filtration and evaporation of solvent gave the title compound in the form of a colorless oil (293 mg), which was purified by a silica gel column (silica 60, 15 g) eluted with ether/pet ether (1/1) to give a colorless oil (223 mg, 0.59 mmol, 83%).

C.
[1β,2α(5Z),3α,4β]-7-[3-[[(Phenylmethoxy)amino]methyl]-7-oxabicyclo[2.2.1]hept-2-yl]-5-heptenoic acid 1 N LiOH (6 ml) was added to the title B ester (223 mg, 0.59 mmol) in THF (30 ml) and $H_2O$ 6 ml) at room temperature. After 6 hours stirring at room temperature, the reaction was quenched by addition of 1 N HCl (6 ml) and poured into brine (20 ml). The products were extracted with ether (100 ml×3). The combined ether layers were washed with brine (50 ml×3) and dried over $Na_2SO_4$. Filtration and evaporation of solvent yielded a slightly yellow colored oil (210 mg), which was purified by a silica gel column (silica 60, 20 g)

eluted with CH$_2$Cl$_2$/MeOH (9.4/0.6) to give the title product in the form of a colorless oil (99 mg, 0.27 mmol, 46%).

Analysis Calcd for C$_{21}$H$_{29}$O$_2$N.0.2H$_2$O: C, 69.46; H, 8.16; N, 3.87; Found: C, 69.60; H, 8.17; N, 3.77.

EXAMPLE 5

[1β,2α(5Z),3β,4β]-7-[3-[[(Phenylmethoxy)amino]methyl]-7-oxabicyclo[2.2.1]hept-2-yl]-2-yl]-5-heptenoic acid

A.

[1β,2α(5Z),3β,4β]-7-[3-[[(Phenylmethoxy)imino]methyl]-7-oxabicyclo[2.2.1]hept-2-yl]-5-heptenoic acid, methyl ester O-Benzylhydroxylamine hydrochloride (351.2 mg, 2.2 mmol) was added to a stirred suspension of sodium acetate (196.8 mg, 2.4 mmol) in 10 ml distilled ethanol in an argon atmosphere. A solution of [1β,2α(5Z),3β,4β]-7-[3-formyl-7-oxabicyclo[2.2.1]hept-2-yl]-5-heptenoic acid, methyl ester prepared as described in Example 1, Part A, (532 mg, 2 mmol) in 1 ml ethanol was added and the mixture was stirred at room temperature 90 minutes. The mixture was poured into 100 ml ether and the ether solution was washed with 1 N HCl solution (2×20 ml), saturated NaHCO$_3$ solution (2×20 ml) and saturated NaCl solution (2×20 ml). The solution was dried over MgSO$_4$, filtered and taken to dryness in vacuo leaving 730 mg (98%) of oil. This was chromatographed on 35 g silica gel 60, eluting with ether-pet ether (1:2) to give 573 mg (77%) of clean (by TLC) title compound as a colorless oil.

B.

[1β,2α(5Z),3β,4β]-7-[3-[[(Phenylmethoxy)amino]methyl]-7-oxabicyclo[2.2.1]hept-2-yl]-5-heptenoic acid, methyl ester The Part A methyl ester (328 mg, 0.88 mmol) and sodium cyanoborohydride (83.2 mg, 1.32 mmol) were dissolved in methanol (8 ml) and glacial acetic acid (4 ml). The mixture was stirred at room temperature 3¾ hours and then acidified to pH 1 with 1 N HCl solution. After stirring at room temperature 30 minutes, the mixture was basified with NaHCO$_3$. The product was extracted into ether (2×80 ml), washed with saturated NaHCO$_3$ solution and saturated NaCl solution, dried and freed of solvent in vacuo to give 313 mg colorless oil. This was chromatographed on silica gel 60 (20 g), eluting with ether-pet ether to give pure title compound in the form of a colorless oil (292 mg, 89%). TLC:silica gel, ether-pet ether 3:1, vanillin R$_f$=0.33.

C.

[1β,2α(5Z),3β,4β]-7-[3-[[(Phenylmethoxy)amino]methyl]-7-oxabicyclo[2.2.1]hept-2-yl]-5-heptenoic acid The title B methyl ester (292 mg, 0.78 mmol) was dissolved in THF (40 ml) and water (8 ml) and treated with 1 N LiOH solution (7.8 ml). The mixture was stirred at room temperature 6 hours, then treated with 1 N HCl (7.8 ml) and poured into saturated NaCl solution (25 ml). The product was extracted into ether (3×50 ml), dried over MgSO$_4$ and freed of solvent in vacuo leaving 234 mg. This was chromatographed on silicar CC7 (20 g) eluting with CH$_2$Cl$_2$ to give the title product, 191 mg (68%). TLC: silica gel, 6% MeOH in CH$_2$Cl$_2$, vanillin R$_f$=0.2.

Analysis Calcd for C$_{21}$H$_{29}$O$_4$N: C, 70.17; H, 8.13; N, 3.90; Found: C, 70.31; H, 8.00; N, 3.93.

EXAMPLE 6

(1β,2α,3β,4β)-7-[3-[(Phenylmethoxy)amino]methyl]-7-oxabicyclo[2.2.1]hept-2-yl]heptanoic acid Following the procedure of Example 3 and Example 5 except substituting O-benzylhydroxylamine hydrochloride for hexylamine, the title compound is obtained.

EXAMPLE 7

[1β,2α(5Z),3β,4β]-7-[3-(Heptylamino)-7-oxabicyclo[2.2.1]hept-2-yl]-5-heptenoic acid

A.

[1β,2α(5Z),3β,4β]-7-[3-Carboxyl-7-oxabicyclo[2.2.1]hept-2-yl]-5-heptenoic acid, methyl ester To 5.3 g (19.9 mmole) of [1β,2α(5Z),3β,4β]-7-[3-(hydroxymethyl)-7-oxabicyclo[2.2.1]hept-2-yl]-5-heptenoic acid, methyl ester prepared as described in U.S. Pat. No. 4,143,054 in 300 ml of dimethylformamide was added 26.2 g (69.7 mmole, 3.5 eq) of pyridinium dichromate. The reaction was stirred for 24 hours, diluted with 300 ml of water and extracted with three 200 ml portions of ether. The ethereal layer was washed with three 100 ml portions of water and dried over anhydrous magnesium sulfate. The crude product was purified by flash chromatography using LP-1 silica and a gradient of 20% ether in pentane to 40% ether in pentane to provide 800 mg (15.0%) of the title acid.

B.

[1β,2α(5Z),3β,4β]-7-[3-Amino-7-oxabicyclo[2.2.1]hept-2-yl]-5-heptenoic acid, methyl ester To 295.3 mg (1.04 mmole) of the title A acid in 3 ml of anhydrous toluene was added 169 mg (1.04 mmole, 1 eq) of carbonyldiimidazole at 25° under an argon atmosphere. The reaction was stirred for 1 hour and 230.4 mg (2.08 mmole, 2 eq) of trimethylsilylazide was added. The reaction mixture was stirred for an additional 3 hours, diluted with 25 ml of toluene and washed successfully with 10 ml of cold 5% potassium bisulfate, and 10 ml of brine and dried over anhydrous magnesium sulfate. This organic solution was filtered, concentrated in vacuo, and diluted with 15 ml of anhydrous toluene. The solution was refluxed for 1 hour at 90°.

The toluene solution was then concentrated in vacuo, placed under an argon atmosphere, diluted with a 25% solution of 0.1 N HCl in THF and stirred for 18 hours. The reaction mixture was diluted with 50 ml of water and washed with 50 ml of ether. The aqueous solution was then neutralized with saturated NaHCO$_3$, extracted with two 100 ml portions of ethyl acetate, washed with brine and dried over anhydrous magnesium sulfate to provide 131 mg (49%) of the title amine as an oil.

C.

[1β,2α(5Z),3β,4β]-7-[3-(Heptylamino)-7-oxabicyclo[2.2.1]hept-2-yl]-5-heptenoic acid, methyl ester To 130 mg (0.51 mmole) of the title B amine in 3 ml of anhydrous methanol under an argon atmosphere at 25° was added 87.3 mg (0.76 mmole, 1.5 eq) of heptanal and ca. 300 mg of activated crushed 3 Å molecular sieves. This solution was stirred for 55 hours, diluted with 4 ml of anhydrous methanol, cooled to 0°, and an excess of sodium borohydride was added. This reaction was stirred for 30 minutes, quenched with 1 ml of acetone, diluted with 100 ml of ether and washed successively with 50 ml of water, and 50 ml of brine, and dried over anhydrous magnesium sulfate. This material was purified by preparative TLC on a 2 mm 20×20 Merck silica gel-60 F254 plate using 35/3.5/1-chloroform:methanol:88% formic acid as the eluent. A band at $R_f$ 0.5 was eluted with 10% methanol in chloroform to provide 109 mg (60%) of the title ester as an oil.

D.
[1β,2α(5Z),3β,4β]-7-[3-(Heptylamino)-7-oxabicyclo[2.2.1]hept-2-yl]-5-heptenoic acid 109 Mg (0.31 mmole) of the title C ester was diluted with 10 ml of 1 N sodium hydroxide solution and refluxed at 95° for 45 minutes under an argon atmosphere. This solution was cooled, diluted with 10 ml of water and washed with 20 ml of ether. The aqueous layer was acidified to ca. pH 6.5 with dilute hydrochloric acid, extracted with two 100 ml portions of ethyl acetate and dried over anhydrous magnesium sulfate. This material was purified by flash chromatography on an LP-1 silica column using a 10% methanol in methylene chloride solution as the eluent, concentrated in vacuo, diluted with distilled methylene chloride and filtered through a millipore membrane to provide 67.9 mg (40%) of the title product as a light yellow clear oil.

Analysis Calcd for: C, 71.17; H, 10.45; N, 4.15; Calcd. value with 0.29 mole of water: C, 70.08; H, 10.46; N, 4.09; Found: C, 70.08; H, 10.23; N, 3.93.

EXAMPLE 8

[1β,2α(5Z),3α,4β]-7-[3-(Heptylamino)-7-oxabicyclo[2.2.1]hept-2-yl]-5-heptenoic acid

A.
[1β,2α(5Z),3α,4β]-7-[3-Carboxyl-7-oxabicyclo[2.2.1]hept-2-yl]-5-heptenoic acid, methyl ester To 5.3 g (19.9 mmole) of [1β,2α(5Z),3α,4β]-7-[3-(hydroxymethyl)-7-oxabicyclo[2.2.1]hept-2-yl]-5-heptenoic acid, methyl ester prepared as described in U.S. Pat. No. 4,143,054 in 300 ml of dimethylformamide is added 26.2 g (69.7 mmole, 3.5 eq) of pyridinium dichromate. The reaction is stirred for 24 hours, diluted with 300 ml of water and extracted with three 100 ml portions of ether. The ethereal layer is washed with three 100 ml portions of water and dried over anhydrous magnesium sulfate. The crude product is purified by flash chromatography using LP-1 silica and a gradient of 20% ether in pentane to 40% ether in pentane to provide 800 mg (15.0%) of the title acid.

B.
[1β,2α(5Z),3α,4β]-7-[3-Amino-7-oxabicyclo[2.2.1]hept-2-yl]-5-heptenoic acid, methyl ester To 295.3 Mg (1.04 mmole) of the title A acid in 3 ml of anhydrous toluene is added 169 mg (1.04 mmole, 1 eq) of carbonyldiimidazole at 25° under an argon atmosphere. The reaction is stirred for 1 hour and 230.4 mg (2.08 mmole, 2 eq) of trimethylsilylazide is added. The reaction mixture is stirred for an additional 3 hours, diluted with 25 ml of toluene and washed successively with 10 ml of cold 5% potassium bisulfate, and 10 ml of brine and dried over anhydrous magnesium sulfate. This organic solution is filtered, concentrated in vacuo and diluted with 15 ml of anhydrous toluene. The solution is refluxed for 1 hour at 90°.

The toluene solution is then concentrated in vacuo, placed under an argon atmosphere, diluted with a 25% solution of 0.1 N HCl in THF and stirred for 18 hours. The reaction mixture is diluted with 50 ml of water and washed with 50 ml of ether. The aqueous solution is then neutralized with saturated NaHCO₃, extracted with two 100 ml portions of ethyl acetate, washed with brine and dried over anhydrous magnesium sulfate to provide 131 mg (49%) of the title amine as an oil.

C.
[1β,2α(5Z),3α,4β]-7-[3-(Heptylamino)-7-oxabicyclo[2.2.1]hept-2-yl]-5-heptenoic acid, methyl ester To 130 mg (0.51 mmole) of the title B amine in 3 ml of anhydrous methanol under an argon atmosphere at 25° is added 87.3 mg (0.76 mmole, 1.5 eq) of heptanal and ca. 300 mg of activated crushed 3 Å molecular sieves. This solution is stirred for 55 hours, diluted with 4 ml of anhydrous methanol, cooled to 0°, and an excess of sodium borohydride is added. This reaction is stirred for 30 minutes, quenched with 1 ml of acetone, diluted with 100 ml of ether and washed successively with 50 ml of water, and 50 ml of brine, and dried over anhydrous magnesium sulfate. This material is purified by preparative TLC on a 2 mm 20×20 Merck silica gel-60 F254 plate using 35/3.5/1-chloroform:methanol:88% formic acid as the eluent. A band at $R_f$ 0.5 is eluted with 10% methanol in chloroform to provide 109 mg (60%) of the title ester as an oil.

D.
[1β,2α(5Z),3α,4β]-7-[3-(Heptylamino)-7-oxabicyclo[2.2.1]hept-2-yl]-5-heptenoic acid 109 mg (0.31 mmole) of the title C ester is diluted with 10 ml of a 1 N sodium hydroxide solution and refluxed at 95° for 45 minutes under an argon atmosphere. This solution is cooled, diluted with 10 ml of water and washed with 20 ml of ether. The aqueous layer is acidified to ca. pH 6.5 with dilute hydrochloric acid, extracted with two 100 ml portions of ethyl acetate and dried over anhydrous magnesium sulfate. This material is purified by flash chromatography on an LP-1 silica column using a 10% methanol in methylene chloride solution as the eluent, concentrated in vacuo, diluted with distilled methylene chloride and filtered through a millipore membrane to provide 67.9 mg (40%) of the title product as a light yellow clear oil.

EXAMPLE 9

[1β,2α(5Z),3β,4β]-7-[3-(Pentylamino)methyl]-7-oxabicyclo[2.2.1]hept-2-yl]-5-heptenoic acid Following the procedure of Example 1 except substituting pentylamine for hexylamine the title compound is obtained.

EXAMPLE 10

[1β,2α(5Z),3α,4β]-7-[3-(Pentylamino)methyl]-7-oxabicyclo[2.2.1]hept-2-yl]-5-heptenoic acid Following the procedure of Example 2 except substituting pentylamine for hexylamine, the title compound is obtained.

EXAMPLE 11

(1β,2α,3β,4β)-7-[3-(Pentylamino)methyl]-7-oxabicyclo[2.2.1]hept-2-yl]heptanoic acid Following the procedure of Example 3 except substituting pentylamine for hexylamine, the title compound is obtained.

EXAMPLE 12

[1β,2α(5Z),3β,4β]-7-[3-(Heptylamino)methyl]-7-oxabicyclo[2.2.1]hept-2-yl]-5-heptenoic acid Following the procedure of Example 1 except substituting heptylamine for hexylamine, the title compound is obtained.

EXAMPLE 13

[1β,2α(5Z),3α,4β]-7-[3-(Heptylamino)methyl]-7-oxabicyclo[2.2.1]hept-2-yl]-5-heptenoic acid Following the procedure of Example 2 except substituting heptylamine for hexylamine, the title compound is obtained.

EXAMPLE 14

[(1β,2α,3β,4β)-7-[3-(Heptylamino)methyl]-7-oxabicyclo[2.2.1]hept-2-yl]heptanoic acid Following the procedure of Example 3 except substituting heptylamine for hexylamine, the title compound is obtained.

EXAMPLE 15

[1β,2α(5Z),3β,4β]-7-[3-(Pentylamino)-7-oxabicyclo[2.2.1]hept-2-yl]-5-heptenoic acid Following the procedure of Example 7 except substituting pentanal for heptanal, the title compound is obtained.

EXAMPLE 16

[1β,2α(5Z),3α,4β]-7-[3-(Pentylamino)-7-oxabicyclo[2.2.1]hept-2-yl]-5-heptenoic acid Following the procedure of Example 8 except substituting pentanal for heptanal, the title compound is obtained.

EXAMPLE 17

[1β,2α(5Z),3β,4β]-7-[3-(Hexylamino)-7-oxabicyclo[2.2.1]hept-2-yl]-5-heptenoic acid Following the procedure of Example 7 except substituting hexanal for heptanal, the title compound is obtained.

EXAMPLE 18

[1β,2α(5Z),3α,4β]-7-[3-(Hexylamino)-7-oxabicyclo[2.2.1]hept-2-yl]-5-heptenoic acid Following the procedure of Example 8 except substituting hexanal for heptanal, the title compound is obtained.

EXAMPLE 19

(1β,2β,3α,4β)-7-[3-[[2-(1-Oxopentyl)hydrazino]methyl]-7-oxabicyclo[2.2.1]hept-2-yl]heptanoic acid

A. Pentanoyl hydrazine

Methyl valerate (11.62 g, 0.1 mol) was added to hydrazine hydrate (5.0 g, 0.1 mol). The reaction was heated at reflux under vigorous stirring for 24 hours. Low boiling materials (MeOH and H₂O) were removed in vacuo and the residue was crystallized from isopropyl ether to give the title compound in the form of needle crystals (10.5 g, 0.0905 mol, 91%, m.p. 59°–61° C.).

B.

(1β,2β,3β,4β)-7-[3-(Hydroxymethyl)-7-oxabicyclo[2.2.1]hept-2-yl]-heptanoic acid, methyl ester To 800 mg (3.0 mmole) of the [1β,2β(5Z),3β,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate was added, under an argon atmosphere, 400 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title B compound.

C.

(1β,2β,3ξ,4β)-7-[3-Formyl-7-oxabicyclo[2.2.1]hept-2-yl]heptanoic acid, methyl ester To 1.21 g (5.6 mmole, 2.0 equiv.) of pyridinium chlorochromate (PCC) and 20 ml of anhydrous CH₂Cl₂ was added, under an argon atmosphere, 730 mg (2.8 mmole) of the title B alcohol in 2 ml of CH₂Cl₂. The reaction was stirred for 2 hours at 25°, diluted with 100 ml of ether, filtered through a pad of florisil, and evaporated to furnish 670 mg (88%) of the title C compound as a white crystalline solid.

D.

(1β,2β,3α,4β)-7-[3-Formyl-7-oxabicyclo[2.2.1]hept-2-yl]heptanoic acid, methyl ester To 800.0 mg of the title C aldehyde in 20 ml of anhydrous methanol under an argon atmosphere at 25° was added 100 mg of sodium methoxide. The reaction was stirred for 2 hours, diluted with 100 ml of saturated ammonium chloride and extracted with four 100 ml portions of ether. The ethereal layer was washed with 50 ml of brine dried over anhydrous magnesium sulfate and concentrated to afford 765.0 mg (98%) of the title D aldehyde.

E.

(1β,2β,3α,4β)-7-[3-[[(1-Oxopentyl)hydrazono]methyl]-7-oxabicyclo[2.2.1]hept-2-yl]heptanoic acid, methyl ester The title D aldehyde (532 mg, 2 mmol) and the title A hydrazide (255.2 mg, 2.2 mmol) are stirred in EtOH (10 ml) at room temperature for 1 hour. The reaction is poured into Et₂O (150 ml), which is washed with 1 N HCl (30 ml×2), saturated NaHCO₃ (30 ml×2), brine (30 ml×2), and dried over MgSO₄. Filtration and evaporation of solvent give a viscous oil (739 mg), which is purified by silica gel column eluted with Et₂O/EtOAc-4/1 to give a colorless oil (697 mg, 93%). Upon standing, the oil solidifies. Crystallization from diisopropyl ether/pet ether affords colorless needle crystals.

F.

(1β,2β,3α,4β)-7-[3-[[2-(1-Oxopentyl)hydrazino]methyl-7-oxabicyclo[2.2.1]hept-2-yl]heptanoic acid, methyl ester NaBH₃CN (57 mg, 0.92 mmol) is added to a magnetically stirred solution of the title E compound (265 mg, 0.71 mmol) in MeOH (8.5 ml), followed by addition of AcOH (1.5 ml) dropwise. After 2¼ hours stirring at room temperature, additional NaBH₃CN (40 mg, 0.64 mmol) and AcOH (1 ml) is added. Stirring is continued at room temperature for 1 hour. Then, the reaction is quenched by addition of 2 N HCl to pH 1 and stirred for 30 minutes. The reaction is basified by addition of saturated NaHCO3. The products are extracted with Et2O (100 ml×2). The combined ether layers are washed with brine and dried over MgSO4. Filtration and evaporation of solvent gives the title compound in the form of a colorless oil (293 mg), which is purified by a silica gel column (silica 60, 15 g) eluted with ether/pet ether (1/1) to give a colorless oil (223 mg, 0.59 mmol, 83%).

G.
(1β,2β,3α,4β)-7-[3-[[2-1-Oxopentyl)hydrazino]methyl]-7-oxabicyclo[2.2.1]hept-2-yl]-heptanoic acid 1 N LiOH (6 ml) is added to the title F ester (223 mg, 0.59 mmol) in THF (30 ml) and H2O (6 ml) at room temperature. After 6 hours stirring at room temperature, the reaction is quenched by addition of 1 N HCl (6 ml) and poured into brine (20 ml). The products are extracted with ether (100 ml×3). The combined ether layers are washed with brine (50 ml×3) and dried over Na2SO4. Filtration and evaporation of solvent yield a slightly yellow colored oil (210 mg), which is purified by a silica gel column (silica 60, 20 g) eluted with CH2Cl2/MeOH (9.4/0.6) to give the title product in the form of a colorless oil (99 mg, 0.27 mmol), 46%.

EXAMPLE 20

[1β,2α(5Z),3β,4β]-7-[3-[[2-(1-Oxopentyl)hydrazino]-methyl]-7-oxabicyclo[2.2.1]hept-2-yl]-5-heptenoic acid

A.
[1β,2α(5Z),3β,4β]-7-[3-[[(1-Oxopentyl)hydrazono]methyl]-7-oxabicyclo[2.2.1]hept-2-yl]-5-heptenoic acid, methyl ester A solution of the Example 1A aldehyde (532 mg, 2 mmol) and pentanoyl hydrazide (prepared as described in Example 19, Part A) (255.1 mg, 2.2 mmol) in EtOH (10 ml) was stirred at room temperature for 2 hours. The reaction mixture was poured into 100 ml of ether and washed with 1 N HCl (2×20 ml), saturated NaHCO3 solution (2×20 ml) and saturated NaCl solution (2×20 ml). The ether solution was dried over MgSO4, filtered and freed of solvent in vacuo leaving 697 mg (99%) of oil. This was chromatographed on 30 g silica gel 60, eluting with ether to give 514 mg (70%) of the title B compound as a viscous oil. TLC: silica gel, Et2O, vanillin $R_f$=0.17.

B.
[1β,2α(5Z),3β,4β]-7-[3-[[2-(1-Oxopentyl)hydrazino]-methyl]-7-oxabicyclo[2.2.1]hept-2-yl]-5-heptenoic acid, methyl ester Following the procedure of Example 19 Part F but substituting the above Part A hydrazono compound for the Example 21 title E compound, the above title B compound is obtained.

C.[1β,2α(5Z),3β,4β]-7-[3-[[2-(1-Oxopentyl)hydrazino]-methyl]-7-oxabicyclo[2.2.1]hept-2-yl]-5-heptenoic acid Following the procedure of Example 19 Part G but substituting the Part B methyl ester for the Example 22 Part F methyl ester, the title acid product is obtained.

EXAMPLE 21

(1β,2α,3α,4β)-7-[3-[[2-(1-Oxopentyl)hydrazino]methyl]-7-oxabicyclo[2.2.1]hept-2-yl]heptanoic acid

A. Pentanoyl hydrazine

The title compound is prepared as described in Example 19A.

B.
[1β,2α(5Z),3α,4β]-7-[3-[[(1-Oxopentyl)hydrazono]methyl]-7-oxabicyclo[2.2.1]hept-2-yl]-5-heptenoic acid, methyl ester The Example 2A aldehyde (532 mg, 2 mmol) and the title A hydrazide (255.2 mg, 2.2 mmol) were stirred in EtOH (10 ml) at room temperature for 1 hour. The reaction was poured into Et2O (150 ml), which was washed with 1 N HCl (30 ml×2), saturated NaHCO3 (30 ml×2), brine (30 ml×2), and dried over MgSO4. Filtration and evaporation of solvent gave a viscous oil (739 mg), which was purified by silica gel column eluted with Et2O/EtOAc-4/1 to give a colorless oil (697 mg, 93%). Upon standing, the oil solidified. Crystallization from diisopropyl ether/pet ether afforded colorless needle crystals (375 mg out of 482 mg), m.p. 57°–58° C.

Analysis Calcd for $C_{20}H_{32}O_4N_2$: C, 65.91; H, 9.26; N, 7.69; Found: C, 65.61; H, 9.08; N, 7.90

C.
(1β,2α,3α,4β)-7-[3-[[2-(1-Oxopentyl)hydrazino]methyl]-7-oxabicyclo[2.2.1]hept-2-yl]heptanoic acid, methyl ester To 800 mg (2.2 mmole) of the title B hydrazono compound dissolved in 20 ml ethyl acetate is added, under an argon atmosphere, 160 mg of 5% Pd on carbon. The argon atmosphere is exchanged for a slight positive pressure of hydrogen and the reaction is stirred for 8 hours at 25° C., filtered through a celite plug and evaporated to provide 753 mg of the title compound.

D.
(1β,2α,3α,4β)-7-[3-[[2-(1-Oxopentyl)hydrazino]methyl]-7-oxabicyclo[2.2.1]hept-2-yl]heptanoic acid Following the procedure of Example 19 Part G but substituting the Part D methyl ester for the Example 19 Part F methyl ester, the title acid product is obtained.

EXAMPLE 22

[1β,2α,(5Z),3α,4β]-7-[3-[[(Pentyloxy)amino]methyl]-7-oxabicyclo[2.2.1]hept-2-yl]-5-heptenoic acid

A. Ethyl N-hydroxyurethane

H2N-OH.HCl (27.8 g, 0.40 mol) was added portionwise to a solution of Na2CO3 (62.4 gm, 0.59 mol) in H2O (184 ml) under vigorous magnetic stirring. The reaction was endothermic and gave a white solid suspension. Then, ethyl chloroformate (42.4 g) was added dropwise at 0° C. in an ice bath. After completing the addition, the reaction was warmed to room temperature and stirring was continued for 1.5 hours. The reaction was acidified to pH 2 by addition of concentrated HCl. The products were extracted into Et2O by a continuous liquid-liquid extractor (24 hours). The ether layer was dried over MgSO4. Filtration and evaporation of solvent in vacuo yielded the title compound in the form of a clear yellow oil (37.3 g, 0.355 mol, 89%). The crude product was pure enough for a next reaction, so that no purification was attempted.

B. Ethyl O-pentyl-N-hydroxyurethane

KOH (6.6 g, 0.12 mol) dissolved in EtOH (30 ml) was added to 1-bromopentane (15.4 g, 0.1 mol) and ethyl N-hydroxyurethane (prepared as described in Part A, 10.5 g, 0.1 mol). The reaction was heated at reflux for 6 hours. The reaction was poured into ether (400 ml), and the resulting solids were filtered. The filtrate was washed with saturated NH$_4$Cl and dried over MgSO$_4$. Filtration and evaporation of solvents in vacuo gave a colorless liquid (14.3 g) which was distilled to afford the title compound in the form of a colorless oil (10.6 g, 0.061 mol, b.p. 91° C./2.75 mHg, 61%).

C. O-pentylhydroxyamino hydrochloride

Ethyl O-pentyl-N-hydroxyurethane, prepared as described in Part B, (10.6 g, 0.061 mol) and KOH (13.6 g, 0.242 mol) in H$_2$O (65 ml) were heated at reflux for 4 hours. The products were extracted into ether (150 ml×3). The combined ether layers were washed with 2 N HCl (100 ml). Then, the water layer was washed with Et$_2$O (100 ml) and evaporated off in vacuo to give white solid (6.8 g). MeOH (50 ml) was added to dissolve most of the solid. Undissolved solid was removed by filtration and the filtrate was evaporated in vacuo to give the title compound in the form of a white solid (6.5 g, 46 mmol, 77%).

D.
[1β,2α(5Z),3α,4β]-7-[3-[[(Pentyloxy)imino]methyl]-7-oxabicyclo[2.2.1]hept-2-yl]-5-heptenoic acid, methyl ester O-pentylhydroxyamino hydrochloride (306.9 mg, 2.2 mmol) was added to a suspension of NaOAc (196.8 mg, 2.4 mmol) in dry EtOH (10 ml). NaCl was immediately precipitated out. Then, aldehyde prepared as described in Example 2, Part A (532 mg, 2.0 mmol) in dry EtOH (1 ml) was added at room temperature. After 1 hour stirring, the reaction mixture was poured into Et$_2$O, which was washed with 1 N HCl (20 ml×2), saturated NaHCO$_3$ (20 ml×2), brine (20 ml×2) and dried over MgSO$_4$. Filtration and evaporation of solvents in vacuo gave an oil (689 mg), which was purified by column chromatography (silica 60, 30 g) eluted with ether/pet. ether (1:2) to give the title compound in the form of a colorless oil (fast moving isomer; 575 mg, 1.56 mmol, 78% slow moving isomer; 83 mg, 0.22 mmol, 11%). $^{13}$C NMR spectra indicated that the fast moving isomer was anti-isomer of the oxime and the slow moving isomer was syn-isomer.

E.
[1β,2α(5Z),3α,4β]-7-[3-[[(Pentyloxy)amino]methyl]-7-oxabicyclo[2.2.1]hept-2-yl]-5-heptenoic acid, methyl ester NaBH$_3$CN (57 mg, 0.92 mmol) is added to a magnetically stirred solution of Part D oxime (265 mg, 0.71 mmol) in MeOH (8.5 ml), followed by addition of AcOH (1.5 ml) dropwise. After 2¼ hours stirring at room temperature, additional NaBH$_3$CN (40 mg, 0.64 mmol) and AcOH (1 ml) are added. Stirring is continued at room temperature for 1 hour. Then, the reaction is quenched by addition of 2 N HCl to pH 1 and stirred for 30 minutes. The reaction is basified by addition of saturated NaHCO$_3$. The products are extracted with Et$_2$O (100 ml×2). The combined ether layers are washed with brine and dried over MgSO$_4$. Filtration and evaporation of solvent gave the title compound in the form of a colorless oil (293 mg), which is purified by a silica gel column (silica 60, 15 g) eluted with ether/pet ether (1/1) to give a colorless oil.

F.
[1β,2α(5Z),3α,4β]-7-[3-[[(Pentyloxy)amino]methyl]-7-oxabicyclo[2.2.1]hept-2-yl]-5-heptenoic acid 1 N LiOH (6 ml) is added to the title E ester (223 mg, 0.59 mmol) in THF (30 ml) and H$_2$O (6 ml) at room temperature. After 6 hours stirring at room temperature, the reaction is quenched by addition of 1 N HCl (6 ml) and poured into brine (20 ml). The products are extracted with ether (100 ml×3). The combined ether layers are washed with brine (50 ml×3) and dried over Na$_2$SO$_4$. Filtration and evaporation of solvent yield a slightly yellow colored oil (210 mg), which is purified by a silica gel column (silica 60, 20 g) eluted with CH$_2$Cl$_2$/MeOH (9.4/0.6) to give the title product in the form of a colorless oil.

EXAMPLE 23

(1β,2α,3α,4β)-7-[3-[[(Pentyloxy)amino]methyl]-7-oxabicyclo[2.2.1]hept-2-yl]heptanoic acid

A.
(1β,2α,3α,4β)-7-[3-(Hydroxymethyl)-7-oxabicyclo[2.2.1]hept-2-yl]heptanoic acid, methyl ester To 800 mg (3.0 mmole) of the [1β,2α(5Z),3α,4β]-7-[3-(hydroxymethyl)-7-oxabicyclo[2.2.1]hept-2-yl]-5-heptenoic acid, methyl ester as prepared in U.S. Pat. No. 4,143,054, dissolved in 120 ml of ethyl acetate as added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.
(1β,2α,3α,4β)-7-[3-Formyl-7-oxabicyclo[2.2.1]hept-2-yl]heptanoic acid, methyl ester.

Following the procedure of Example 2A except substituting the part A alcohol for [1β,2α(5Z),3α,4β]-7-[3-(hydroxymethyl)-7-oxabicyclo[2.2.1]hept-2-yl]-5-heptenoic acid, methyl ester, the title compound is obtained.

C.
(1β,2α,3α4β)-7-[3-[[(Pentyloxy)imino]methyl]-7-oxabicyclo[2.2.1]hept-2-yl]heptanoic acid Following the procedure of Example 19 except substituting the Part B aldehyde for the Example 19D aldehyde, the title product is obtained.

D.
[1β,2α,3α,4β]-7-[3-[[(Pentyloxy)amino]methyl]-7-oxabicyclo[2.2.1]hept-2-yl]heptanoic acid, methyl ester NaBH$_3$CN (57 mg, 0.92 mmol) is added to a magnetically stirred solution of Part C oxime (265 mg, 0.71 mmol) in MeOH (8.5 ml), followed by addition of AcOH (1.5 ml) dropwise. After 2¼ hours stirring at room temperature, additional NaBH$_3$CN (40 mg, 0.64 mmol) and AcOH (1 ml) are added. Stirring is continued at room temperature for 1 hour. Then, the reaction is quenched by addition of 2 N HCl to pH 1 and stirred for 30 minutes. The reaction is basified by addition of saturated NaHCO$_3$. The products are extracted with Et$_2$O (100 ml×2). The combined ether layers are washed with brine and dried over MgSO$_4$. Filtration and evaporation of solvent gives the title compound in the form of a colorless oil (293 mg), which is purified by a silica gel column (silica 60, 15 g) eluted with ether/pet ether (1/1) to give a colorless oil.

E.
[1β,2α,3α,4β]-7-[3-[[(Pentyloxy)amino]methyl]-7-oxabicyclo[2.2.1]hept-2-yl]heptanoic acid 1 N LiOH (6 ml) is added to the title F ester (223 mg, 0.59 mmol) in THF (30 ml) and H$_2$O (6 ml) at room temperature. After 6 hours stirring at room temperature, the reaction is quenched by addition of 1 N HCl (6 ml) and poured into brine (20 ml). The products are extracted with ether (100 ml×3). The combined ether layers are washed with brine (50 ml×3) and dried over Na$_2$SO$_4$. Filtration and evaporation of solvent yield a slightly yellow colored oil (210 mg), which is purified by a silica gel column (silica 60, 20 g) eluted with CH$_2$Cl$_2$/MeOH (9.4/0.6) to give the title product in the form of a colorless oil (99 mg, 0.27 mmol), 46%.

EXAMPLE 24

[1β,2α(5Z),3α,4β]-7-[3-[[2-(Propoxycarbonyl)hydrazino]methyl]-7-oxabicyclo[2.2.1]hept-2-yl]-5-heptenoic acid A.
[1β,2α(5Z),3α,4β]-7-[3-[[(Propoxycarbonyl)hydrazono]methyl]-7-oxabicyclo[2.2.1]hept-2-yl]-5-heptenoic acid, methyl ester

[1β,2α(5Z),3α,4β]-7-[3-Formyl-7-oxabicyclo[2.2.1]hept-2-yl]-5-heptenoic acid, methyl ester, prepared as described in Example 2, part A, (532 mg, 2 mmol) and n-propyl hydrazinocarboxylate (prepared by refluxing hydrazine hydrate (1.9 g, 0.038 mmol) and di-n-propyl carbonate (5.3 g, 0.036 mmol) for 43 hours), 283.2 mg, 2.4 mmol, were dissolved in EtOH (10 ml) and the reaction was stirred for 2 hours at room temperature. The reaction was concentrated in vacuo leaving a colorless oil (672 mg), which was purified by silica gel column (silica 60, 30 g) eluted with Et$_2$O/pet ether (3.5/1.5) to give a colorless oil (599 mg, 1.63 mmol, 81%).

B.
[1β,2α(5Z),3α,4β]-7-[3-[[2-(Propoxycarbonyl)hydrazino]methyl]-7-oxabicyclo[2.2.1]hept-2-yl]-5-heptenoic acid, methyl ester Title A compound (351 mg, 0.96 mmol) was dissolved in methanol (9 ml) and sodium cyanoborohydride (90 mg, 1.43 mmol) was added. Glacial acetic acid (4.5 ml) was then added dropwise in 2 minutes. The mixture was stirred at room temperature for 2.5 hours and then acidified to pH 1 with 1 N HCl solution. After stirring at room temperature for 30 minutes the mixture was basified with NaHCO$_3$. The product was extracted into ether (3×60 ml) and washed with saturated NaHCO$_3$ solution (50 ml) and saturated NaCl solution (50 ml), dried (MgSO$_4$) and freed of solvent in vacuo leaving 309 mg of oil. This was chromatographed on silica gel 60 (20 g) to give the title compound as an oil (287 mg, 81%) TLC; silica gel, Et$_2$O, vanillin R$_f$=0.57.

C.
[1β,2α(5Z),3α,4β]-7-[3-[[2-(Propoxycarbonyl)hydrazino]methyl]-7-oxabicyclo[2.2.1]hept-2-yl]-5-heptenoic acid The title B methyl ester (285 mg, 0.77 mmol) was dissolved in THF (40 ml) and water (7 ml) in an argon atmosphere. While stirring, 1 N LiOH solution (7.7 ml) was added and the mixture was stirred at room temperature 4 hours. 1 N HCl solution (7.7 ml) was added to adjust the pH to ~6 and the mixture was poured into saturated NaCl column (200 ml). The product was extracted into ethyl acetate (3×100 ml). The combined ethyl acetate extracts were washed with saturated NaCl solution (4×75 ml), dried (MgSO$_4$) and freed of solvent in vacuo leaving 242 mg oil. This was chromatographed in silicar CC7 (25 g), eluting with 2% MeOH in CH$_2$Cl$_2$ to give the title product (181.4 mg, 66.5%) TLC: silica gel, 8% MeOH in CH$_2$Cl$_2$, vanillin R$_f$=0.35.

Anal. Calcd for C$_{18}$H$_{30}$O$_5$N$_2$: C, 61.00; H, 8.53; N, 7.90; Found: C, 60.95; H, 8.47; N, 7.85

EXAMPLE 25

[1β,2α(5Z),3β,4β]-7-[3-[(Phenylamino)methyl]-7-oxabicyclo[2.2.1]hept-2-yl]-5-heptenoic acid Following the procedure of Example 1 except substituting aniline for hexylamine, the title product is obtained.

EXAMPLE 26

[1β,2α(5Z),3α,4β]-7-[3-[(Phenylamino)methyl]-7-oxabicyclo[2.2.1]hept-5-heptenoic acid Following the procedure of Example 2 except substituting aniline for hexylamine, the title product is obtained.

EXAMPLE 27

(1β,2α,3β,4β)-7-[3-[(Phenylamino)methyl]-7-oxabicyclo[2.2.1]hept-2-yl]heptanoic acid Following the procedure of Examples 3 and 1 except substituting aniline for hexylamine, the title product is obtained.

EXAMPLE 28

[1β,2α(5Z),3β,4β]-7-[3-(Benzylamino)-7-oxabicyclo[2.2.1]hept-2-yl]-5-heptenoic acid Following the procedure of Example 7 except substituting benzaldehyde for heptanal, the title compound is obtained.

EXAMPLE 29

[1β,2α(5Z),3β,4β]-7-[3-[(Benzylamino)methyl]-7-oxabicyclo[2.2.1]hept-2-yl]-5-heptenoic acid Following the procedure of Example 1 except substituting benzylamine for hexylamine, the title product is obtained.

EXAMPLE 30

[1β,2α(5Z),3α,4β]-7-[3-[(Benzylamino)methyl]-7-oxabicyclo[2.2.1]hept-2-yl]-5-heptenoic acid Following the procedure of Example 2 except substituting benzylamine for hexylamine, the title product is obtained.

EXAMPLE 31

(1β,2α,3β,4β)-7-[3-[(Benzylamino)methyl]-7-oxabicyclo[2.2.1]hept-2-yl]heptanoic acid Following the procedure of Examples 3 and 1 except substituting benzylamine for hexylamine, the title product is obtained.

EXAMPLE 32

[1β,2α(5Z),3β,4β]-7-[3-(Phenethylamino)-7-oxabicyclo[2.2.1]hept-2-yl]-5-heptenoic acid Following the procedure of Example 7 except substituting benzeneacetaldehyde for heptanal, the title compound is obtained.

EXAMPLE 33

[1β,2β,3α,4β]-7-[3-[[2-(Phenylcarbonyl)hydrazino]methyl]-7-oxabicyclo[2.2.1]hept-2-yl]heptanoic acid Following the procedure of Example 19 except substituting benzoyl hydrazine for pentanoyl hydrazine, the title product is obtained.

EXAMPLE 34

[1β,2α(5Z),3β,4β]-7-[3-[[2-(Phenylcarbonyl)hydrazino]methyl]-7-oxabicyclo[2.2.1]hept-2-yl]-5-heptenoicacid Following the procedure of Example 20 except substituting benzoyl hydrazine for pentanoyl hydrazine, the title product is obtained.

EXAMPLE 35

(1β,2β,3α,4β)-7-[3-[[2-(Benzylcarbonyl)hydrazino]methyl]-7-oxabicyclo[2.2.1]hept-2-yl]heptanoic acid Following the procedure of Example 19 except substituting phenylacetyl hydrazine for pentanoyl hydrazine, the title compound is obtained.

EXAMPLE 36

[1β,2α(5Z),3β,4β]-7-[3-[[2-(Benzylcarbonyl)hydrazino]methyl]-7-oxabicyclo[2.2.1]hept-2-yl]-5-heptenoic acid Following the procedure of Example 20 except substituting phenylacetyl hydrazine for pentanoyl hydrazine, the title compound is obtained.

EXAMPLE 37

(1β,2β,3α,4β)-7-[3-[[2-(Phenoxycarbonyl)hydrazino]methyl]-7-oxabicyclo[2.2.1]hept-2-yl]heptanoic acid Following the procedure of Example 19 except substituting phenoxycarbonyl hydrazine for pentanoyl hydrazine, the title product is obtained.

EXAMPLE 38

[1β,2α(5Z),3β,4β]-7-[3-[[2-(Phenoxycarbonyl)hydrazino]methyl]-7-oxabicyclo[2.2.1]hept-2-yl]-5-heptenoic acid Following the procedure of Example 20 except substituting phenoxycarbonyl hydrazine for pentanoyl hydrazine, the title compound is obtained.

EXAMPLE 39

(1β,2β,3α,4β)-7-[3-[[2-(Benzyloxycarbonyl)hydrazino]methyl]-7-oxabicyclo[2.2.1]hept-2-yl]heptanoic acid Following the procedure of Example 19 except substituting benzyloxycarbonyl hydrazine for pentanoyl hydrazine, the title product is obtained.

EXAMPLE 40

[1β,2α(5Z),3β,4β]-7-[3-[[2-(Benzyloxycarbonyl)hydrazino]methyl-7-oxabicyclo[2.2.1]hept-2-yl]-5-heptenoic acid Following the procedure of Example 20 except substituting benzyloxycarbonyl hydrazine for pentanoyl hydrazine, the title compound is obtained.

EXAMPLE 41

(1β,2β,3α,4β)-7-[3-[[2-(Phenylalanyl)hydrazino]methyl]-7-oxabicyclo[2.2.1]hept-2-yl]heptanoic acid Following the procedure of Example 19 except substituting phenylalanyl hydrazine for pentanoyl hydrazine, the title product is obtained.

EXAMPLE 42

[1β,2α(5Z),3β,4β]-7-[3-[[2-(Phenylalanyl)hydrazino]methyl]-7-oxabicyclo[2.2.1]hept-2-yl]-5-heptenoic acid Following the procedure of Example 20 except substituting phenylalanyl hydrazine for pentanoyl hydrazine, the title compound is obtained.

EXAMPLE 43

(1β,2β,3α,4β)-7-[3-[[2-(Phenylaminocarbonyl)hydrazino]methyl]-7-oxabicyclo[2.2.1]hept-2-yl]heptanoic acid Following the procedure of Example 19 except substituting 4-phenylsemicarbazide for pentanoyl hydrazine, the title compound is obtained.

EXAMPLE 44

[1β,2α(5Z),3β,4β]-7-[3-[[2-(Phenylaminocarbonyl)hydrazino]methyl]-7-oxabicyclo[2.2.1]hept-2-yl]-5-heptenoic acid Following the procedure of Example 20 except substituting 4-phenylsemicarbazide for pentanoyl hydrazine, the title compound is obtained.

EXAMPLE 45

(1β,2β,3α,4β)-7-[3-[[2-(Propylaminocarbonyl)hydrazino]methyl]-7-oxabicyclo[2.2.1]hept-2-yl]heptanoic acid Following the procedure of Example 19 except substituting 4-propylsemicarbazide for pentanoyl hydrazine, the title product is obtained.

EXAMPLE 46

[1β,2α(5Z),3β,4β]-7-[3-[[2-(Propylaminocarbonyl)methyl]-7-oxabicyclo[2.2.1]hept-2-yl]-5-heptenoic acid Following the procedure of Example 20 except substituting 4-propylsemicarbazide for pentanoyl hydrazine, the title compound is obtained.

What is claimed is:

1. A compound having the structural formula

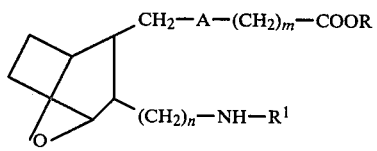

and including all stereoisomers thereof;

wherein A is CH=CH or $(CH_2)_2$;

m is 1 to 8; n is 0 to 5; R is H or lower alkyl; and $R^1$ is lower alkyl, aryl, aryl-lower alkyl, lower alkoxy, aryl-lower alkoxy or

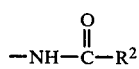

wherein $R^2$ is lower alkyl, lower alkoxy, aryl, aryl-lower alkyl, aryloxy, aryl-lower alkoxy, lower alkylamino, arylamino or aryl-lower alkylamino, the term "aryl" when defining an $R^1$ and/or $R^2$ substituent or when present as part of an $R^1$ and/or $R^2$ substituent may be the same or different and is defined as phenyl, naphthyl, phenyl substituted with lower alkyl, halogen or lower alkoxy, or naphthyl substituted with lower alkyl, halogen or lower alkoxy.

2. The compound as defined in claim 1 having the formula

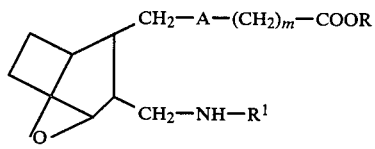

wherein $R^1$ is lower alkyl, lower alkoxy, aryl-lower alkyl or

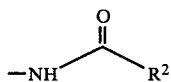

including all stereoisomers thereof.

3. The compound as defined in claim 1 having the formula

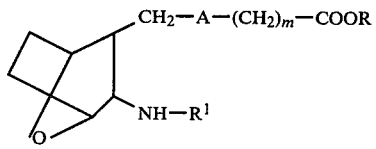

wherein $R^1$ is lower alkyl or aryl-lower alkyl including all stereoisomers thereof.

4. The compound as defined in claim 2 wherein A is CH=CH.

5. The compound as defined in claim 4 wherein $R^1$ is pentyl, hexyl or heptyl.

6. The compound as defined in claim 1 having the name [1β,2α(5Z),3β,4β]-7-[3-[(hexylamino)methyl]-7-oxabicyclo[2.2.1]hept-2-yl]-5-heptenoic acid or the methyl ester thereof or all stereoisomers thereof.

7. The compound as defined in claim 1 having the name [1β,2α(5Z),3β,4β]-7-(heptylamino)-7-oxabicyclo[2.2.1]hept-2-yl]-5-heptenoic acid or the methyl ester thereof or all stereoisomers thereof.

8. The compound as defined in claim 1 having the name [1β,2α(5Z),3α, 4β]-7-[3-[[(phenylmethoxy)amino]methyl]-7-oxabicyclo[2.2.1]hept-2-yl]-5-heptenoic acid or the methyl ester thereof or all stereoisomers thereof.

9. The compound as defined in claim 1 having the name [1β,2α(5Z),3β,4β]-7-[3-[[(phenylmethoxy)amino]methyl]-7-oxabicyclo[2.2.1]hept-2-yl]-5-heptenoic acid or the methyl ester thereof or all stereoisomers thereof.

10. The compound as defined in claim 1 having the name [1β,2α(5Z),3α,4β]-7-[3-[[2-(propoxycarbonyl)hydrazino]methyl]-7-oxabicyclo[2.2.1]hept-2-yl]-5-heptenoic acid, its methyl ester or all stereoisomers thereof.

11. A method of inhibiting platelet aggregation and bronchoconstriction, which comprises administering to the circulatory system of a mammalian host an effective amount of a compound as defined in claim 1 or a pharmaceutically acceptable salt thereof.

12. The method as defined in claim 10 wherein said compound is administered in an amount within the range of from about 1 to about 100 mg/kg.

13. A composition for inhibiting platelet aggregation and bronchoconstriction comprising an effective amount of a compound as defined in claim 1 or a pharmaceutically acceptable salt thereof, and a pharmaceutically acceptable carrier therefor.

14. A method of inhibiting platelet aggregation which comprises administering to a mammalian host an effective amount of a compound as defined in claim 1 or a pharmaceutically acceptable salt thereof.

15. A method of inhibiting bronchoconstriction associated with asthma, which comprises administering to a mammalian host an effective amount of a compound as defined in claim 1 or a pharmaceutically acceptable salt thereof.

* * * * *